(12) United States Patent
Keldmann et al.

(10) Patent No.: US 7,661,425 B2
(45) Date of Patent: Feb. 16, 2010

(54) INHALER

(75) Inventors: Troels Keldmann, Horsholm (DK);
Erik Keldmann, Odense SV (DK);
Teresa Pallotta, Segrate (IT); Flavio Meoli, Agno (CH)

(73) Assignee: Direct Haler A/S (DK)

( * ) Notice: Subject to any disclaimer, the term of this patent is extended or adjusted under 35 U.S.C. 154(b) by 610 days.

(21) Appl. No.: 10/595,445

(22) PCT Filed: Oct. 14, 2004

(86) PCT No.: PCT/DK2004/000701

§ 371 (c)(1),
(2), (4) Date: Apr. 20, 2006

(87) PCT Pub. No.: WO2005/037354

PCT Pub. Date: Apr. 28, 2005

(65) Prior Publication Data

US 2008/0190423 A1    Aug. 14, 2008

(30) Foreign Application Priority Data

Oct. 21, 2003   (DK) ............................... 2003 01547

(51) Int. Cl.
*A61M 11/00* (2006.01)

(52) U.S. Cl. ............................ 128/203.15; 128/203.23

(58) Field of Classification Search ............ 128/203.15, 128/207.14, 911, 912, 203.12, 203.23
See application file for complete search history.

(56) References Cited

U.S. PATENT DOCUMENTS

| 5,797,392 A * | 8/1998 | Keldmann et al. ..... 128/203.15 |
| 6,648,848 B1 * | 11/2003 | Keldmann et al. ............. 604/57 |

FOREIGN PATENT DOCUMENTS

| EP | 1238680 | 9/2002 |
| GB | 2270293 | 3/1994 |
| WO | WO 9622802 | 8/1996 |
| WO | WO 9853869 | 12/1998 |

* cited by examiner

*Primary Examiner*—Steven O Douglas
(74) *Attorney, Agent, or Firm*—Brooks Kushman P.C.

(57) ABSTRACT

An inhaler comprising a tubular body (1) defining a tubular air flow passage with a bendable section, preferably a U-shaped section comprising peripherally extending corrugations and means for supplying a dose of at least one active inhalable, particulate substance into the flow passage and a cap (2). According to the invention the dose of the at least one active, inhalable particulate substance is placed in the cap (2) to be released from said cap substantially at the beginning of the corrugations in the intake direction.

18 Claims, 19 Drawing Sheets

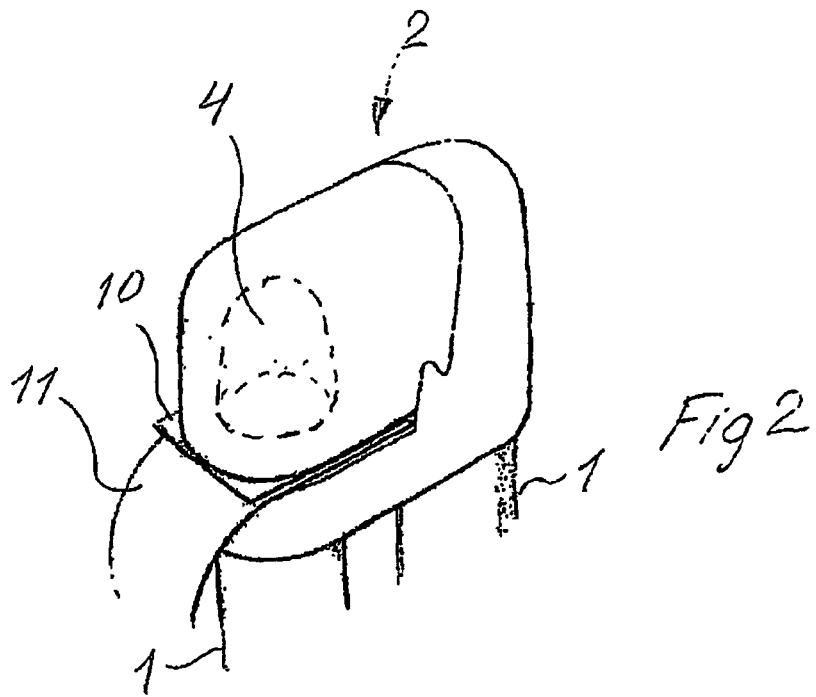
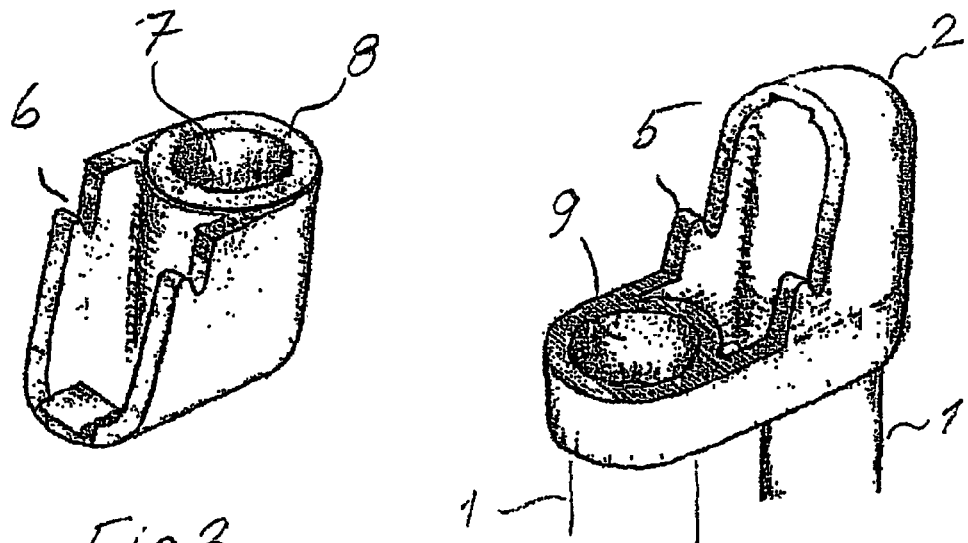

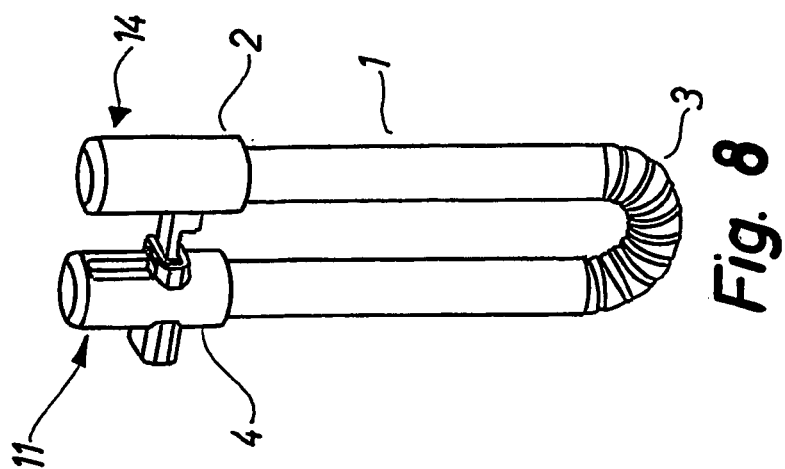
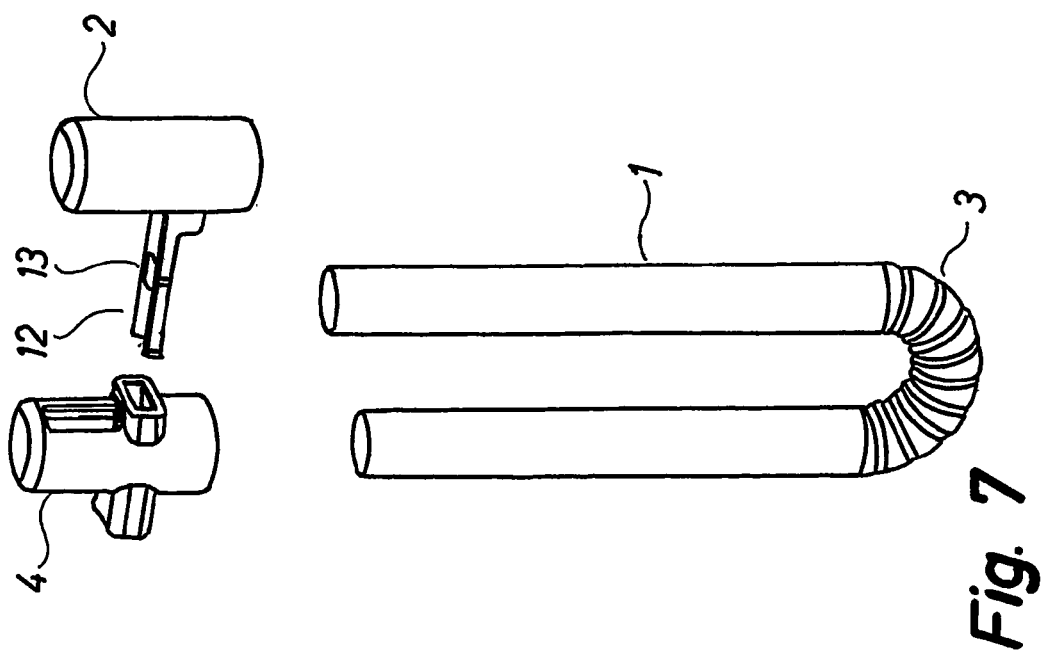

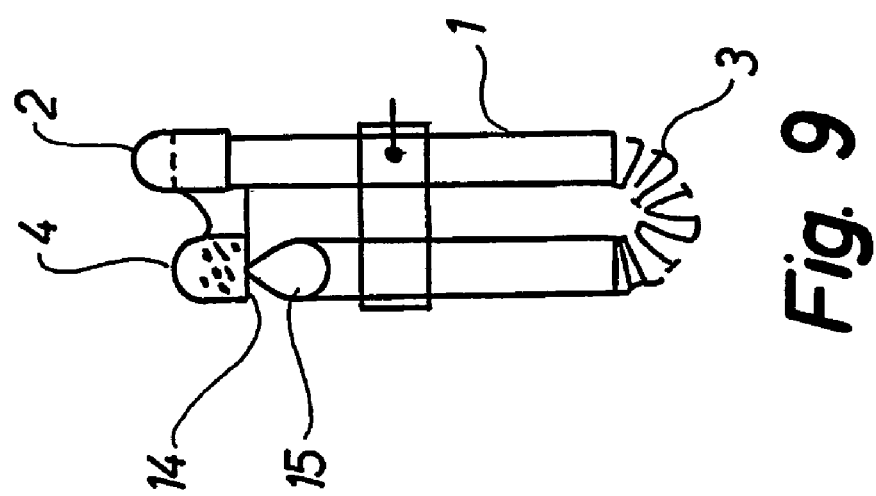

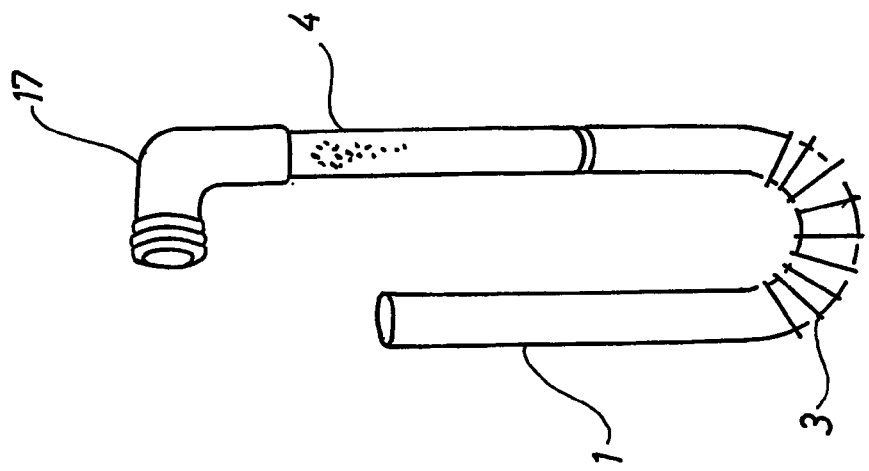
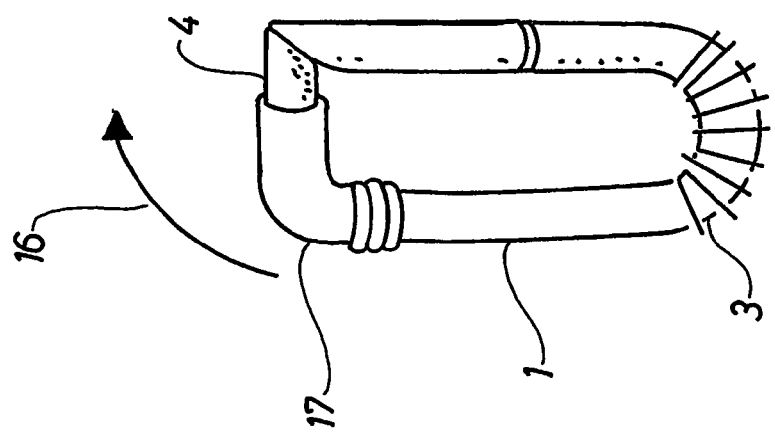

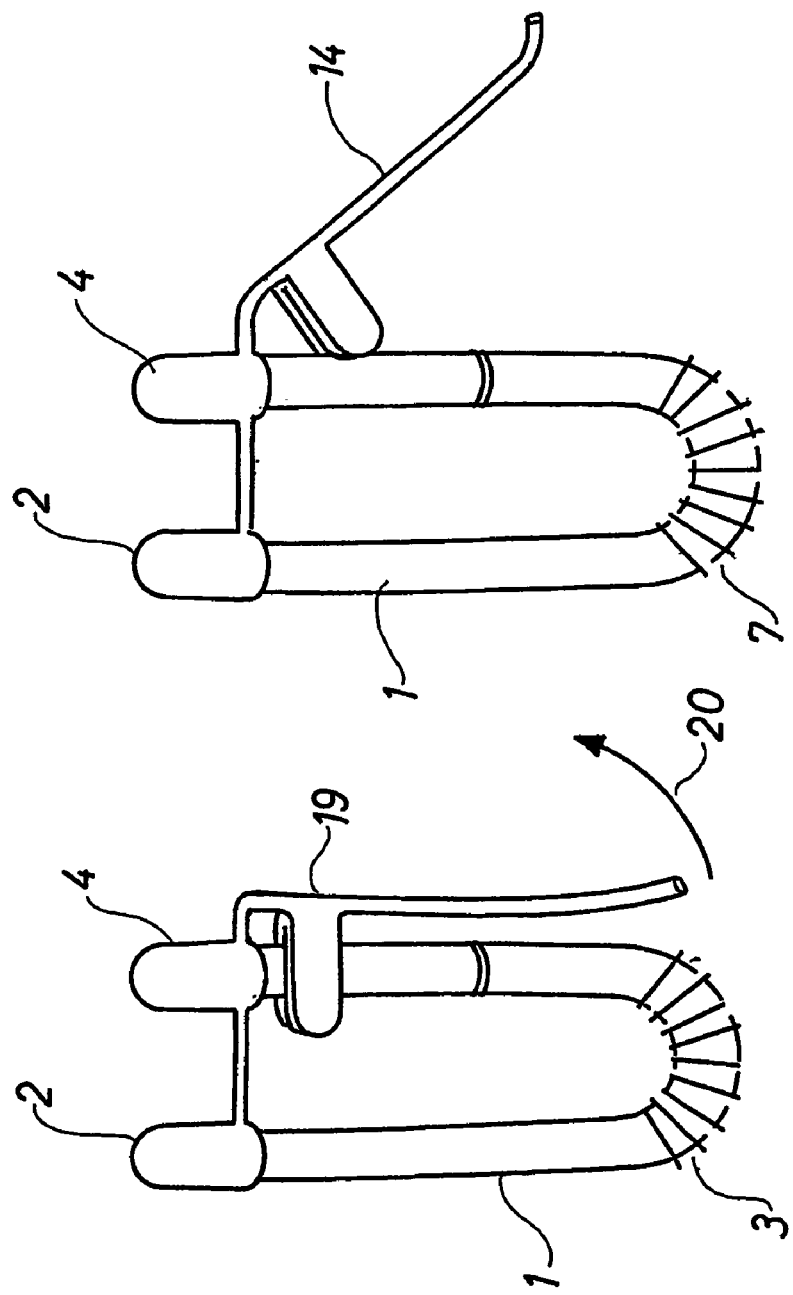

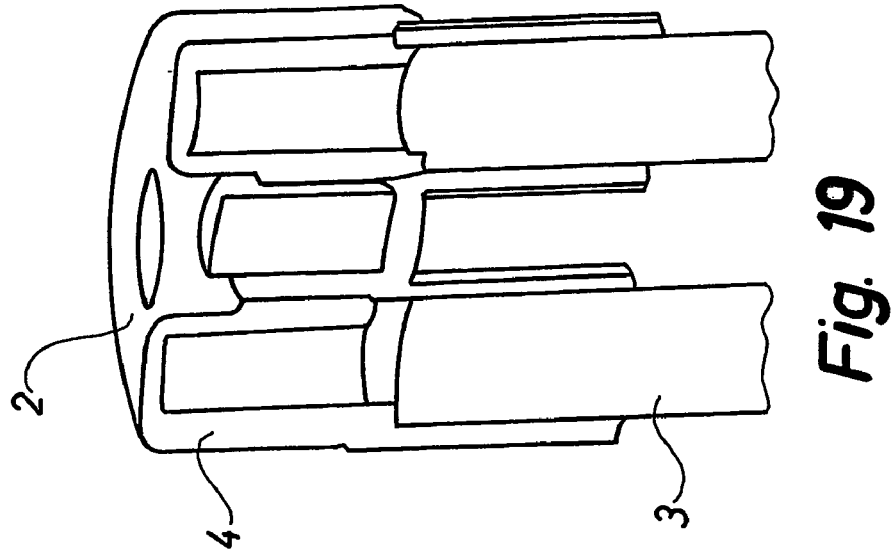
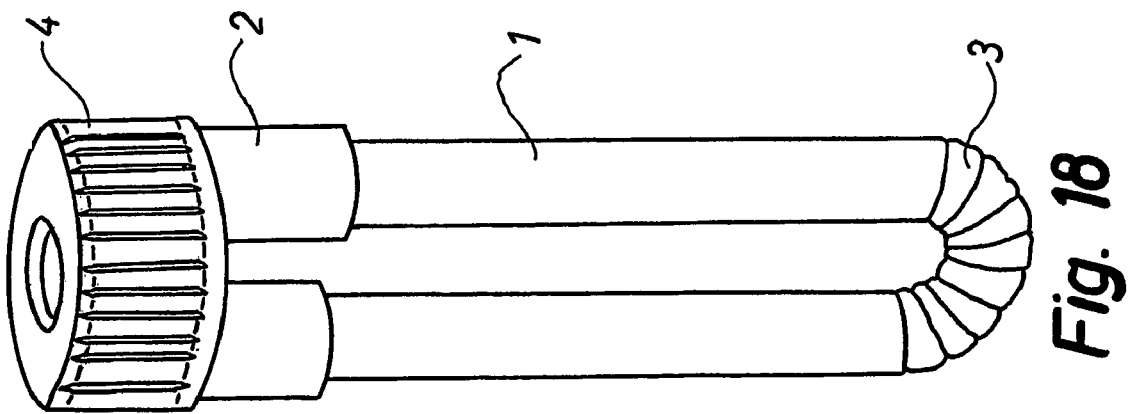

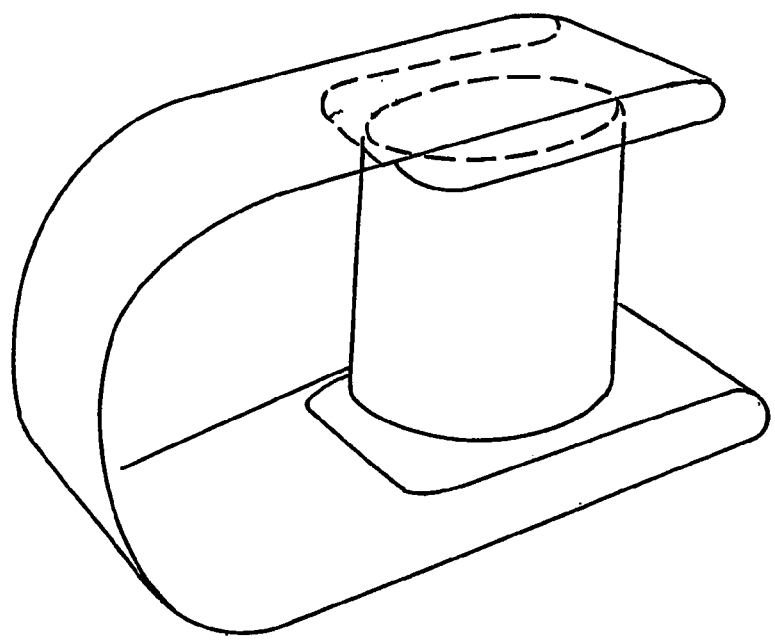
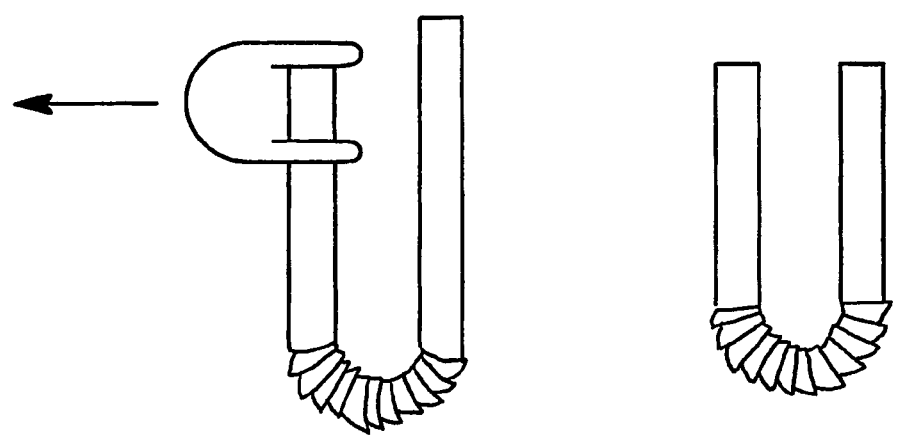
Fig. 24

1/3 of corrugations

2/3 of corrugations

3/3 of corrugations

INHALER

The present invention relates to an inhaler according to the preamble of claim 1. Such an inhaler is useful for a one-time-use-and-dispose-means for supplying a dose of an active, inhalable, particulate substance.

TECHNICAL BACKGROUND

WO 96/22802 discloses an inhaler of the above-mentioned type for pulmonary inhalation comprising a tubular body in which an air flow passage is defined. The inhaler comprises only a single dose of an active, inhalable, particulate substance arranged within the air flow passage, said dose being sealed or closed in relation to the ambient atmosphere by closure means which are to be removed or opened by a user prior to use, the inhaler being intended to be used only once. WO 98/53869 discloses a similar tubular body for nasal inhalation.

The closure means of the known inhaler can be caps at each free end of the tubular body, either as two separate caps or as a two integrated twin caps, in case the tubular body is bent to a position with the free ends closely adjacent.

The single dose contained in the inhaler is a particulate material, normally including one or more pharmaceutically active agents, if appropriate, together with conventional pharmaceutically acceptable additives. In the known single dose inhaler, the particulate material often has a volume substantially smaller than the inner volume of the inhaler between the two caps. Because the volume of said particulate material is substantially smaller than the inner volume of the inhaler, said particulate material may be moved and shaken in the inhaler tube during transport and storage, which at least in case of certain preparations, may lead to alterations of particle size, composition of the particulate substances due to segregation, disintegration and crumbling. Further, it is possible that mechanical impact such as shaking will cause the individual grains of the particulate material to stick together or to the inner walls of the tubular body, thus yielding undesired mechanical properties or incorrect dosage. Such alterations may change the inhalation behaviour of the particulate material, jeopardizing the correct administration of the pharmaceutical agent.

SUMMARY OF THE INVENTION

The object of the invention is to provide an inhaler of the above type, in which the above problems are substantially reduced or fully eliminated. This is obtained by an inhaler according to the characterising clause of claim 1. By having the inhalable, particulate substance in a cap, two objects are obtained. Firstly, the tubular body with the corrugations may be used for dispensing inhalable, particulate substances of an unspecified type, and a generic store of these may be maintained by a user, a pharmacist, a hospital, etc. It is therefore just a matter of attaching the cap including a specific, inhalable, particulate substance to the tubular body and dispense the inhalable, particulate substance into the tubular body. Secondly, by having the inhalable, particulate substance in the cap, it is easier to prevent movement of the inhalable, particulate substance, thus reducing or preventing alterations to it. The essential feature, however, is that the particulate substance is supplied so as to be positioned at the beginning of the corrugated section before inhalation. As a result, the lumps of the particulate substrate due to the hittings of subsequent corrugations before inhalation will be crushed and dispersed more and more into finer particles every time they hit one of the succeeding corrugations. As a result, a far more improved powder dispersion is obtained than hitherto known, the fraction of respirable particles being increased.

According to the invention the cap may comprise at least one closed compartment containing the active, inhalable, particulate substance, the tubular body or said cap comprising means for dispensing said at least one particulate substance by opening, breaking or piercing said at least one closed compartment. Having one or more closed compartments in the cap, it is possible to supply one or more pharmaceutically active agents, which can or cannot be stored together. Further, means are provided, said means being capable of opening the closed compartment and thus facilitating the dispensation of said agents into the tubular body at the beginning of the corrugations.

Furthermore, according to the invention the cap may comprise at least one attachable part comprising at least one closed compartment containing an active, inhalable, particulate substance. In this manner, a combination approach can be used where several, different, pharmaceutically active agents may be used for a single treatment.

Moreover, according to the invention the at least one closed compartment may be closed by means of a tear-off foil, said tear-off foil being adapted to be removed after the at least one attachable part is attached to the cap. By closing the compartment by means of a tear-off foil, and adapting the tear-off foil to be removed after the at least one attachable part is attached to the cap, the risk of contamination is reduced, and the closed compartment is easily opened for dispensing.

Further, according to the invention the at least one closed compartment may be closed by means of a slidable element with at least one hole, in which said slidable element has a first and a second position, said slidable element in said first position being adapted to close said closed compartment, and in said second position being adapted to open said closed compartment by communicating said closed compartment with said hole, said slidable element comprising friction elements adapted to hold said slidable element in the first position to produce some friction, while said slidable element is moved from said first position to said second position, said slidable element being fixed at said second position. When the closed compartment is closed by the slidable element, the compartment can easily be opened for dispension, simply by applying pressure thereto, e.g. by the use of the thumb and index finger. The slidable element may be provided with special pads for applying the pressure. By adding friction elements, e.g. in the form of roughening surfaces or a hole/pin-arrangement it is possible, on the one hand, to secure that the closed compartment is not accidentally opened, and, on the other hand, to ensure that a used cap is not accidentally reused.

Further, according to the invention the closed compartment may be closed by a pierceable foil, the tubular body being adapted to pierce said foil, when the cap is attached to said tubular body. The tubular body may be adapted to pierce the foil, e.g. by cutting it at an angle much like the straws used by cartons for juice and chocolate milk.

Further, according to the invention the closed compartment may be closed by attaching the cap to the tubular body and bending said tubular body, said closed compartment being opened by unbending said tubular body, and means being provided to keep the tubular body bent, while not in use. Bending the tubular body causes a portion of the tubular body to be squeezed off and creates a closed compartment at the end.

This closed compartment may then be reopened simply by straightening the tubular body. By providing means for keeping the tubular body bent, an accidental dispension of the inhalable, particulate substance is prevented.

Further, according to the invention the closed compartment may be closed by providing means squeezing together a part of the tubular body, said closed compartment being opened by removing said means. The means squeezing the tubular body may be in the form of a clothes pin, a fork or other.

Further, according to the invention the closed compartment may comprise a tube-like body, one end of which being permanently closed, while the other end being adapted to be inserted into the tubular body, said closed compartment being closed by means sticking a part of the walls of said tube-like body together, said closed compartment can be opened by adding pressure to or pulling at said tube-like body. The one end of the tubular body is permanently closed by glue, welding, melting or other means ensuring no reusable force to open it. The walls are stuck together in such a manner that if pressure is applied thereto, e.g. from the thumb or index finger, the compartment will open.

Further, according to the invention the at least one closed compartment may be closed by means of a rotating, slidable element with at least one hole, said rotating, slidable element having a first and a second position, and said rotating, slidable element in said first position being adapted to close said closed compartment, and in said second position being adapted to open said closed compartment by communicating said closed compartment with said hole, said rotating, slidable element comprising friction elements, said friction elements being adapted to hold said rotating, slidable element in the first position to produce some friction, while said rotating, slidable element is rotated from said first position to said second position and fixate said rotating, slidable element at said second position. When the closed compartment has a rotating, slidable element, a simple screw-like motion will open the closed compartment. Likewise with the slidable element mentioned above, the friction elements provide means against accidental opening of the closed compartment and accidental reuse.

According to the invention the cap may be constructed from a soft, squeezable material, and the closed compartment may likewise be constructed from a soft, squeezable material, said closed compartment being adapted to rupture, when pressure is applied to said cap, and the material of the closed compartment being adapted in such a manner that, when it ruptures, the material is not dispensed to the tubular body. In this embodiment the closed compartment is, in many ways, similar to the bubbles in bubble-wrap used in protective envelopes. When pressure is applied to the cap, e.g. with the thumb and index finger, the bubble containing the inhalable, particulate substance and the inhalable particulate substance is dispensed to the tubular body. A special advantage is when the bubble is manufactured with a shaped, weak spot, the bubble will rupture in a known way, and none of the material of the bubbles will end up in the tubular body.

Finally, according to the invention the cap may be adapted to accommodate two or more of the tubular bodies. In this manner, two inhalable, particulate substances can be sucked in at the same time through the mouth.

BRIEF DESCRIPTION OF THE DRAWINGS

The invention will be described below with reference to the examples shown in the drawings, in which FIGS. 2-4 show a cap with an attachable, closed compartment for an inhaler according to the invention, FIGS. 7-9 show different ways of sealing and opening the closed compartment, FIGS. 10-14 show embodiments, in which the closed compartment is closed by bending the tubular body, FIGS. 15 and 16 show an embodiment, in which the closed compartment is created by squeezing together a part of the tubular body, FIGS. 18 and 19 show an embodiment similar to the one shown in FIGS. 5 and 6, FIG. 24 shows an inhaler having a cap with a weld-on foil in both ends.

DETAILED DESCRIPTION

Figure 1:
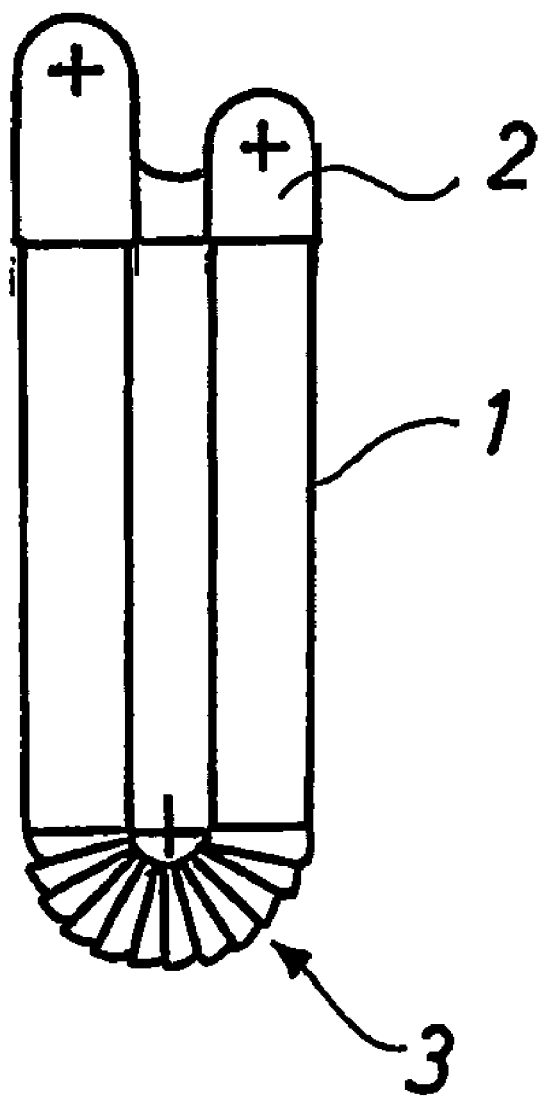
FIG. 1 shows a known inhaler configuration.

As shown in FIG. 1, the known inhaler comprises a tubular body 1 and a cap 2. The tubular body 1 has a corrugated middle section 3 creating a whirl chamber and allowing it to be bent at an angle. The corrugations are substantially sawtooth formed. The inhaler may be used as a pulmonary inhaler or as a nasal inhaler. If it is used as a nasal inhaler, one end of the tubular body 1 should be easily inserted into the mouth and the other end into one nostril of a patient. Simply by blowing through the tubular body 1, the contents of the tubular body 1 will enter the nose.

The cap 2 shown in FIG. 2 for an inhaler according to the invention has a closed compartment 4 containing a pharmaceutically active agent in the form of an inhalable, particulate substance. As mentioned above, transport and handling of the inhaler may cause unwanted effects to sensitive components on the particulate substance. Having the particulate substance in a small closed compartment 4 as illustrated in FIG. 3, much of the mechanical agitation of the particulate substance is prevented, thereby reducing or eliminating the adverse effects. When the cap 2 is placed on the tubular body 1, means 10, 11 are provided for opening the closed compartment 4 and for dispensing the particulate substance into the tubular body 1 at the beginning of the corrugations ready for inhalation.

As shown in FIG. 2, the closed compartment 4 may be provided as a separate unit attachable to the cap 2 by attachment means 5, 6. These attachment means 5, 6 fix the closed compartment 4 in place, usually in a non-removable manner. This has the advantage that the pharmaceutically active agent can be supplied separately, and one inhalator may be used for many different medications. The closed compartment 4 has an inner space 7 and an opening 8 as shown in FIG. 3. The inner space 7 is then filled with the particulate substance, and means are provided for closing and opening the closed compartment 4. The attachment means 5, 6 of the closed compartment 4 matches the cap 2, and when the closed compartment 4 is opened, the opening 8 of the closed compartment 4 is in communication with an opening 9 of the cap 2, allowing the particulate substance to be dispensed into the tubular body 1.

The general principle of the inhaler according to the invention has now been described. What remains to be described are ways by which the closed compartment 4 is closed and opened in use.

As shown in FIG. 2, one embodiment of the closed compartment 4 is closed by a tear-off foil 10. This tear-off foil 10 is composed of a laminate barrier foil such as a layer of aluminium covered by a layer of polypropylene on both sides, said tear-off foil 10 being attached to the opening 8 of the closed compartment 4 shown in FIG. 3. By pulling at the foil 10, which is bent 180°, said foil is separated from the opening 8, and the opening 8 of the closed compartment 4 is in communication with the opening 9. The tear-off foil 10 is provided with an end 11, allowing the foil 10 to be torn off, when the closed compartment 4 is attached to the cap 2 simply by pulling at the end 11.

As a result the particulate substance in the closed compartment 4 is protected against moisture without needing additional packaging for moisture protection, which is of importance to moisture sensitive formulations.

Figure 5:
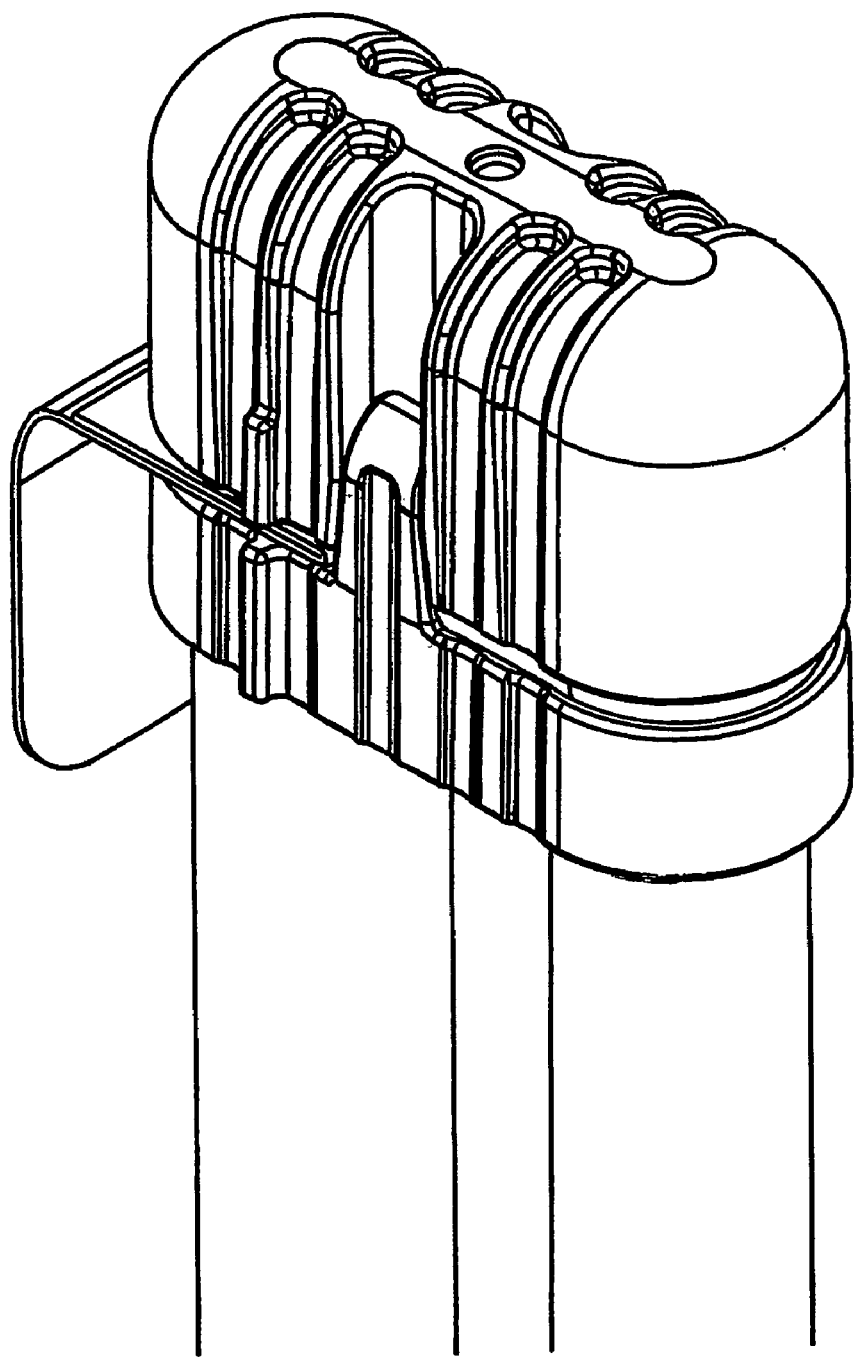
FIGS. 5 and 6 show a cap with an attachable, closed compartment in an alternative embodiment.
Figure 6:
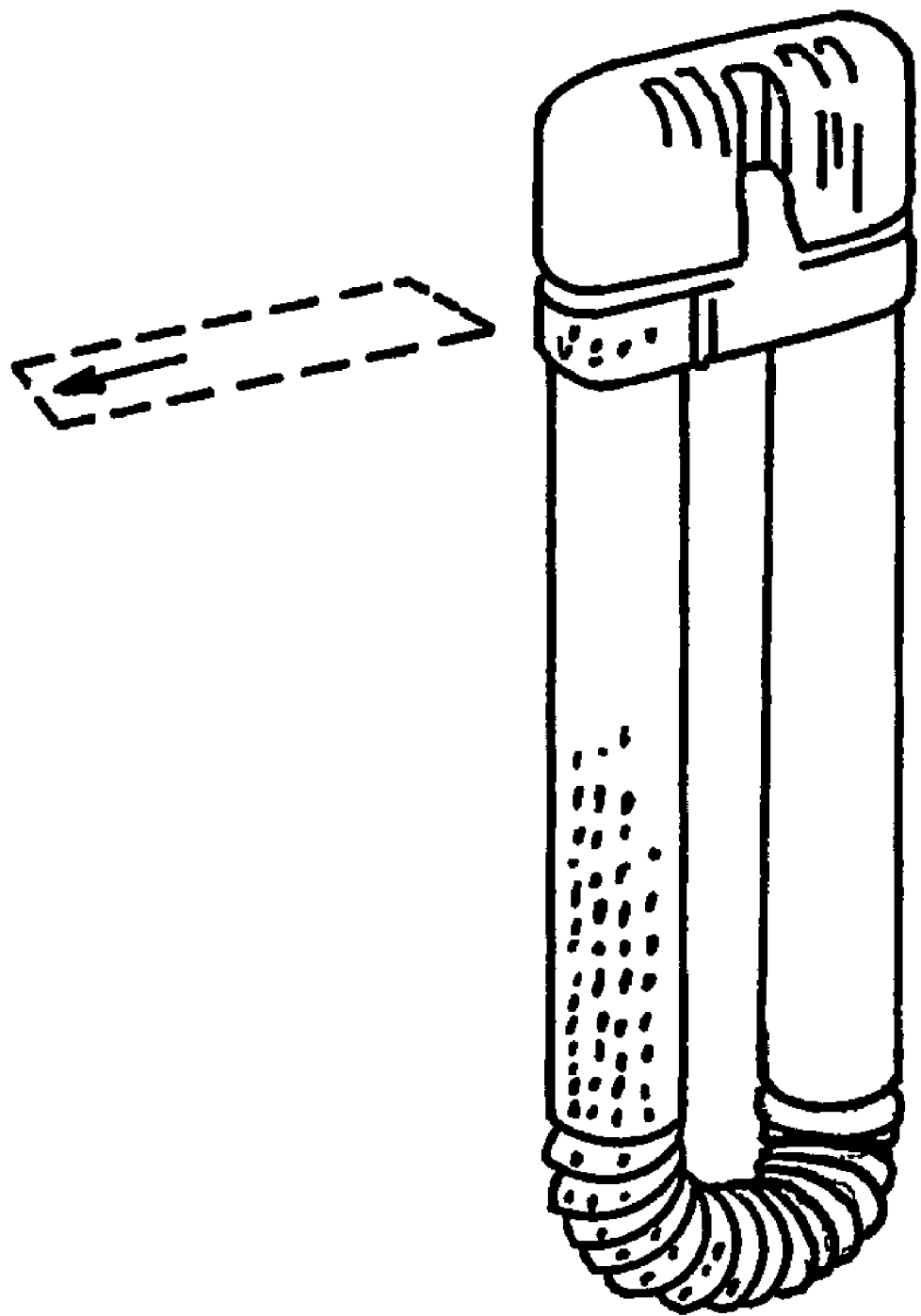
Figure 14:
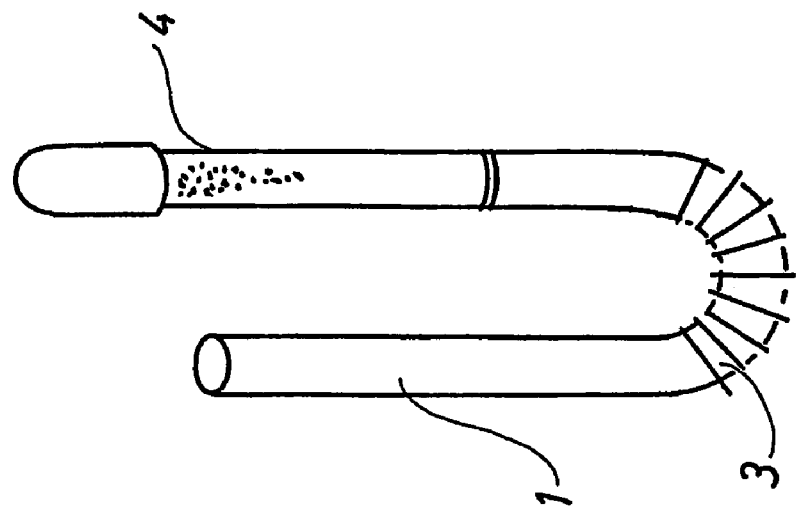
Figure 13:
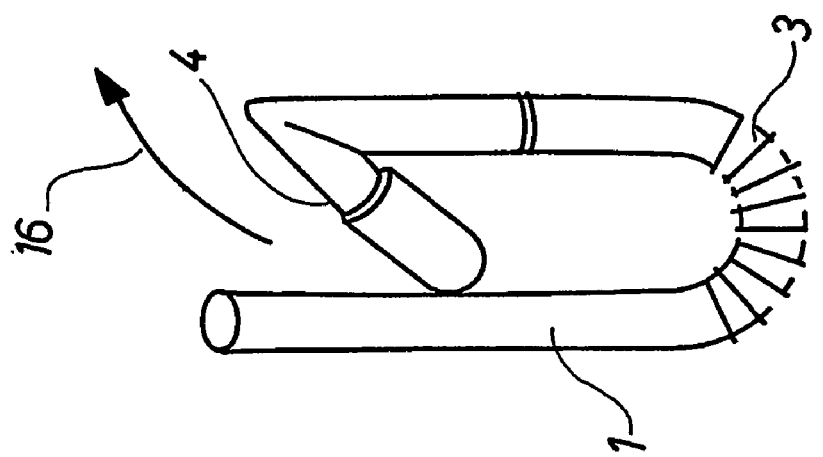
Figure 12:
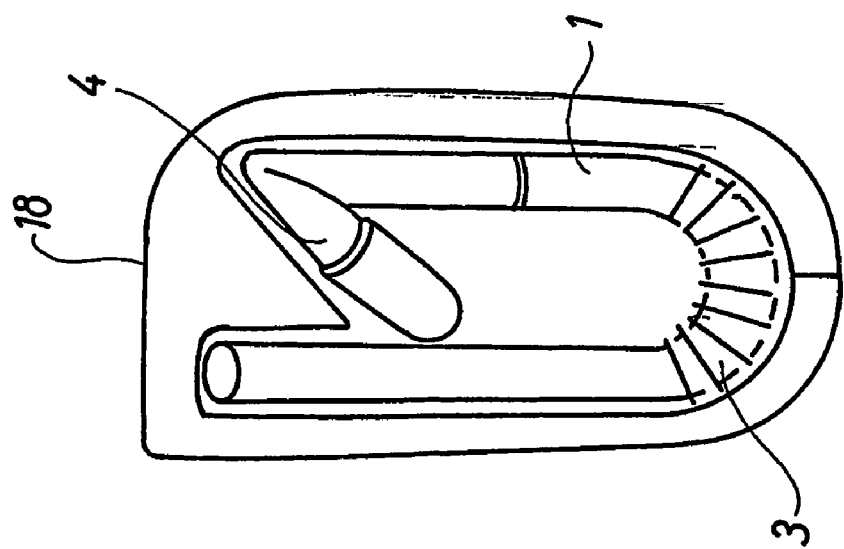

FIGS. 5 and 6 show a cap with an attachable, closed compartment in an alternative embodiment consisting of two portions, a lower portion and an upper portion. The lower portion is to be mounted on the U-shaped inhaler tube and the upper portion with the closed compartment including the particulate substance is to be clipped to the lower portion by means of extending hooks on the lower portion, said hooks engaging corresponding notches in the upper portion. The particulate substance is released by removing the tear-off foil. This embodiment is better suited for mass production than the embodiment shown in FIGS. 2-4.

FIGS. 7 and 8 show an embodiment, in which the closed compartment 4 is closed by a slidable element 12 with a hole. In a first position, the slidable element 2 closes the closed compartment 4, and in a second position the hole 13 of the slidable element 12 is in communication with the closed compartment 4, allowing the particulate substance to be dispensed. The slidable element 12 can be provided with means for pushing it or, as shown, be moved by pushing the cap 2 and the closed compartment 4 together in the direction of the arrows 14. Alternatively, the closed compartment 4 may be opened by pulling the cap 2 and the closed compartment 4 apart. The cap 2 and the closed compartment 4 may be provided with means for helping and pushing them together, e.g. in the form of push-pads, or the like. The slidable element 12 may be provided with friction elements, e.g. in the form of roughened surfaces or by providing pins and holes, locking the cap 4 and the slidable element 12 together and requiring an amount of force to overcome. This has the advantage that the risk of accidental opening of the closed compartment 4 is lessened and prevents accidental reuse of a cap 2.

FIG. 9 shows an embodiment, in which the closed compartment 4 is closed by a piercable material 14. When the cap 2 is attached to the tubular body 1, the end 15 of the tubular body 1 pierces the piercable material 14. The piercing of the piercable material 14 may be helped by shaping the end 15 of the tubular body 1, e.g. by making a diagonal cut to it. This is not unlike how a straw pierces the membrane of a juice carton.

FIGS. 10-14 show embodiments, in which the closed compartment 4 is closed by bending the tubular body 1 and thereby squeezing off a part thereof. The closed compartment 4 is then opened simply by straightening the tubular body 1 in the direction of the arrow 16. The tubular body 1 is provided with means 17, 18 for keeping the tubular body 1 bent while not in use, e.g. by a fastening device 17 holding the ends of the tubular body 1 together or by placing the tubular body 1 in a holder 18, maintaining the bent position.

FIGS. 15 and 16 show an embodiment, in which the closed compartment is created by squeezing together a part of the tubular body 1 by using a squeezing device 19. When the squeezing device 19 is pulled in the direction of the arrow 20 afterwards, the closed compartment 4 opens.

Figure 17:
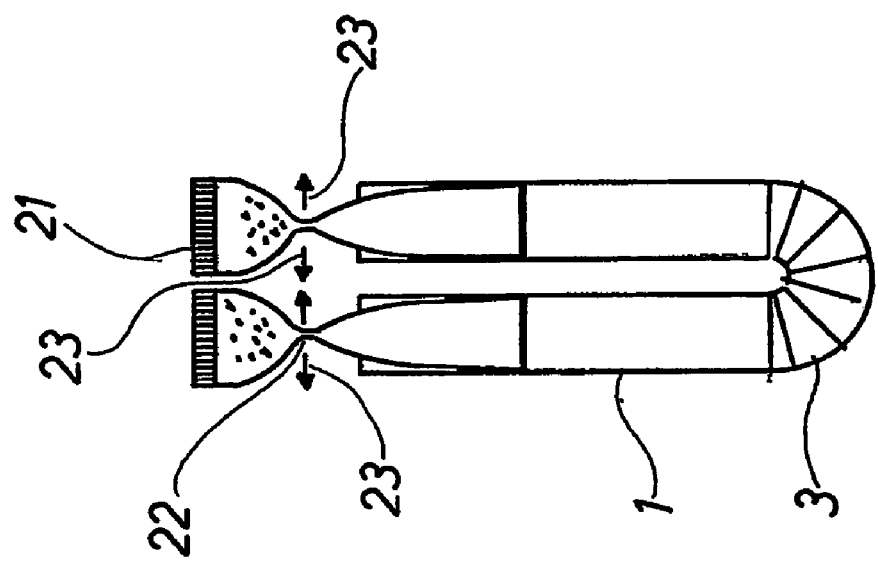
FIG. 17 shows an embodiment, in which the closed compartment is formed by first closing the outer end of the tubular body by gluing, welding or a similar technique.

FIG. 17 shows an embodiment, in which the closed compartment 4 is formed by first closing the outer end of the tubular body 1 by gluing, welding, melting or a similar technique. An outer seal 21 is created and can only be broken by tearing the material of the tubular body 1. A bit further along the tubular body 1 a second seal 22 is created. This seal 22 is weaker than the outer seal 21 and can be opened by applying force in the direction of the arrows 23. This force can be created by applying pressure, e.g. with the thumb and index finger, in a plane perpendicular to the plane of the paper.

FIGS. 18 and 19 show an embodiment almost similar to the one shown in FIGS. 5 and 6. The difference is that the motion is a rotating rather than a translating, and the closed compartment 4 is opened by twisting the cap 2.

Figures 20, 21:
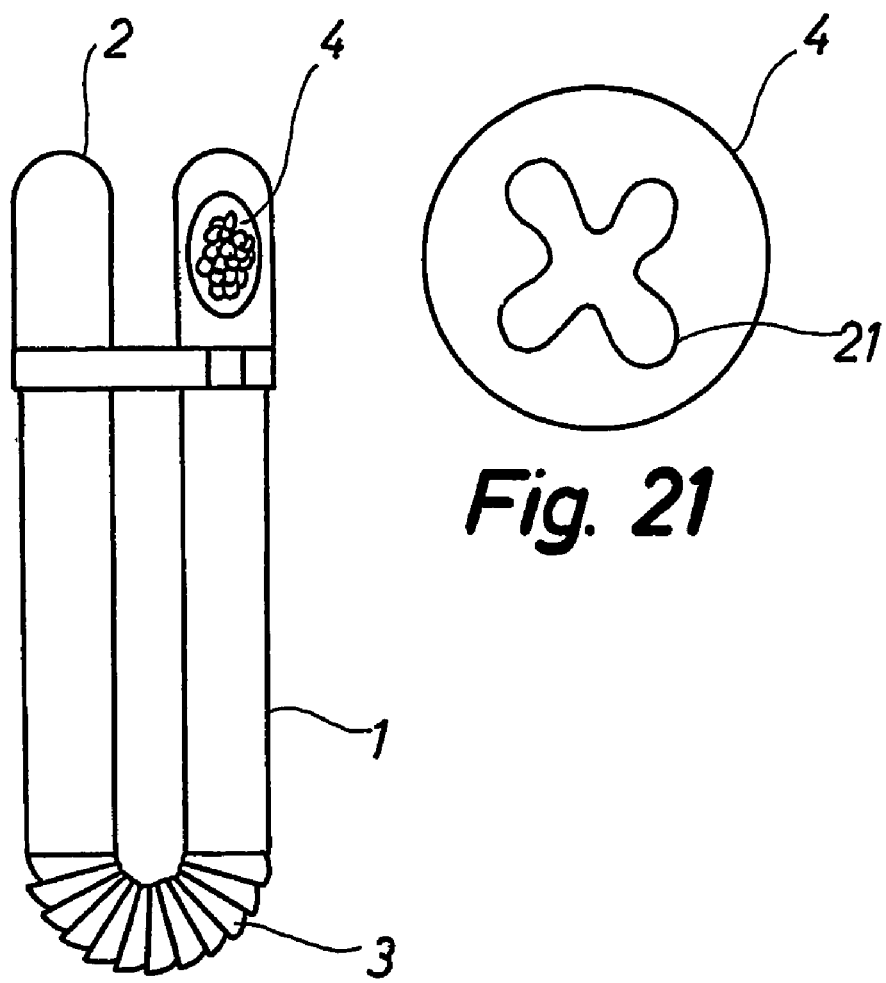
FIG. 20 shows an embodiment, in which the closed compartment is designed to rupture.
FIG. 21 shows the weakened area of the closed compartment seen from below.

FIG. 20 shows an embodiment, in which the cap 2 and the closed compartment 4 are constructed from a soft, squeezable material. When pressure is applied to the cap 2, e.g. with the thumb and an index finger, the closed compartment 4 is designed to rupture, allowing the particulate substance contained therein to be dispensed to the tubular body 1. In this embodiment the design of the closed compartment 4 is not unlike the bubbles used in bubble-wrap for protective envelopes.

FIG. 21 shows the closed compartment 4 from below. The closed compartment 4 may be provided with a special weakened area 24, ensuring rupture of the closed compartment 4 in a known manner, and that the material of the closed compartment 4 does not accidentally end up inside the tubular body 1.

Figure 22:
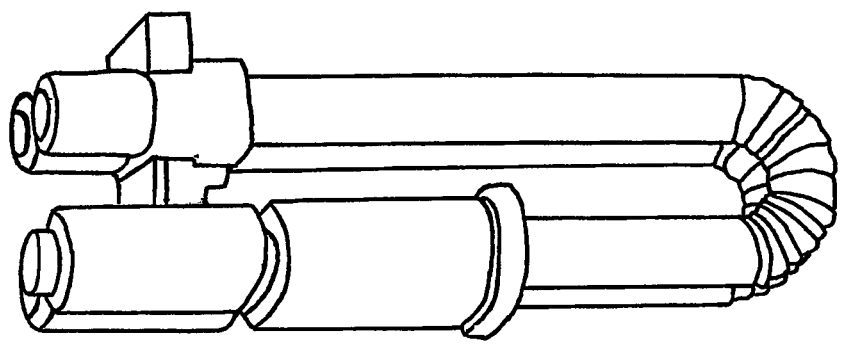
FIGS. 22 and 23 show an inhaler assembly comprising more than one inhaler according to the invention.
Figure 23:
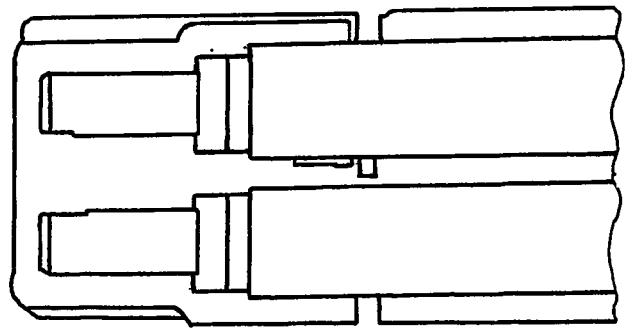

FIGS. 22 and 23 show a special, multi-tube inhaler comprising more than one inhaler according to the invention. Each of the inhalers can be any of the above types, but the multi-tube arrangement permits inhalation of different pharmaceutically active agents through the mouth, use of larger doses, use of pharmaceutical agents having incompatible storage requirements or any number of other reasons.

FIG. 24 shows an embodiment of an inhaler, in which the closed compartment including the particulate substance is closed by means of both ends of the tear-off foil.

Figure 25:
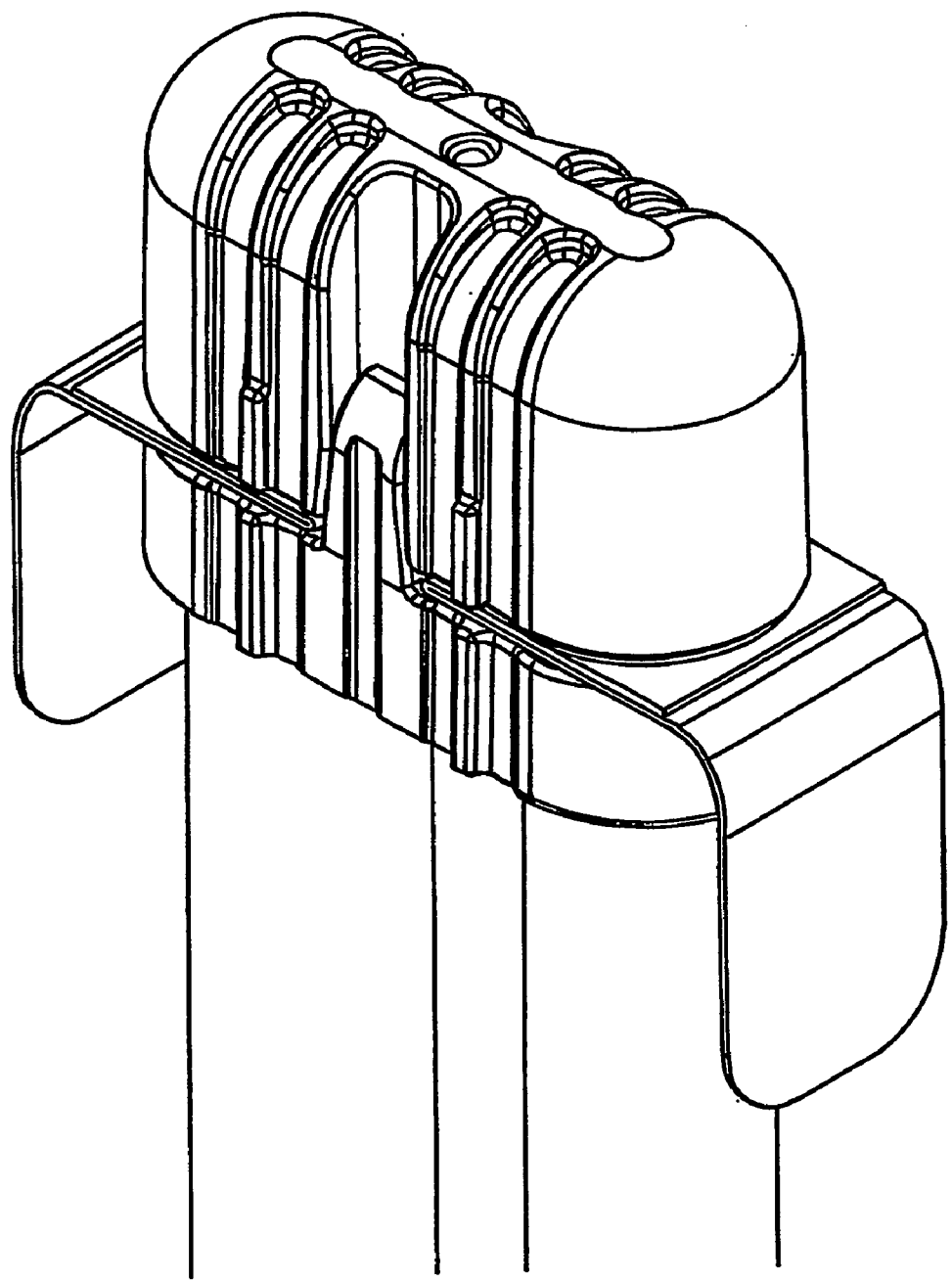
FIG. 25 shows a cap having two closed compartments, and one tear-off foil for each compartment.

FIG. 25 shows an embodiment of an inhaler comprising a tubular body closed by a cap, part of which being closed by means of one weld-on foil at each end so as to provide two closed compartments, each for the at least one active, particulate substance.

Figure 26:
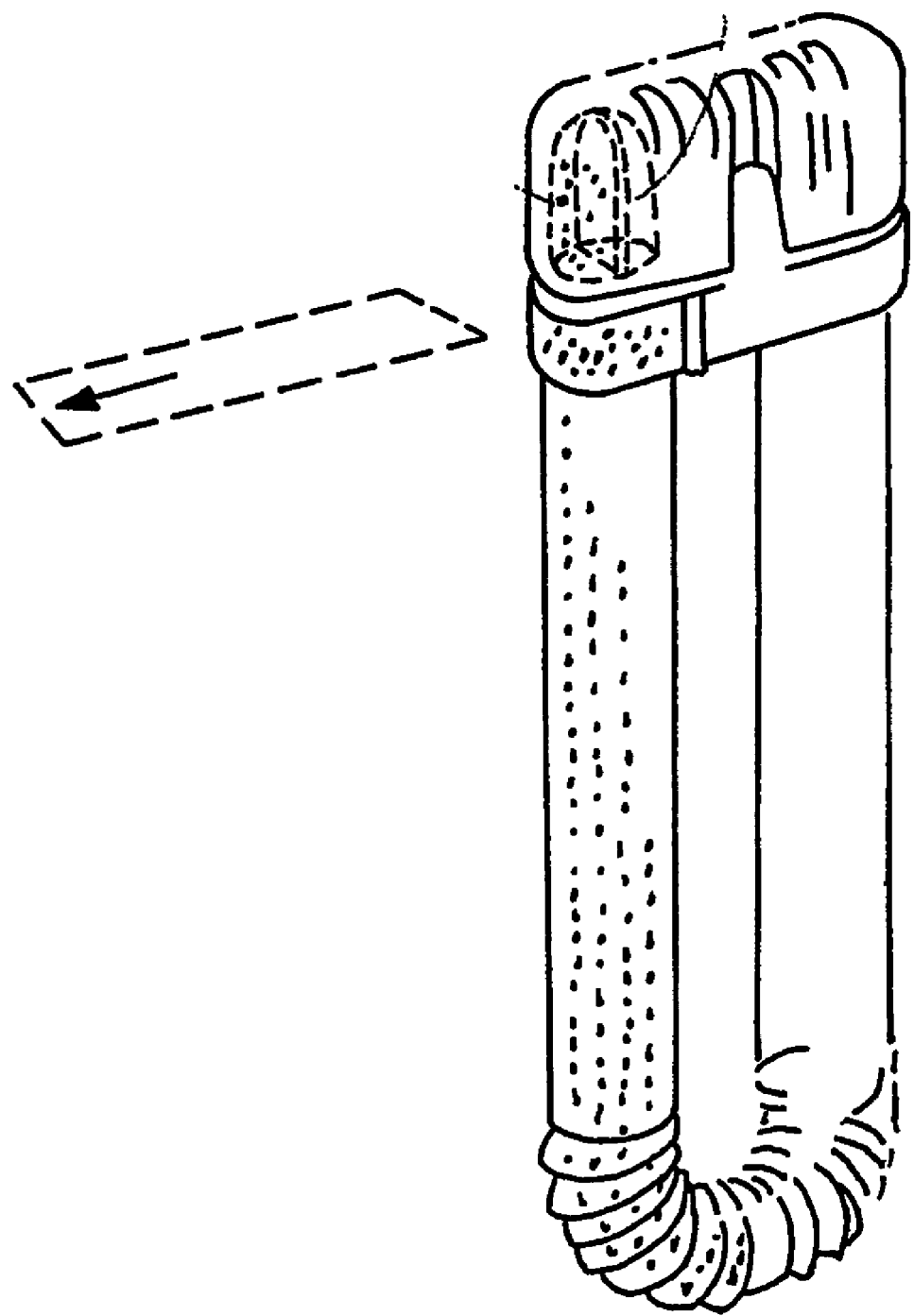
FIG. 26 shows a cap having two closed compartments, and a common tear-off foil or both compartments.

FIG. 26 shows a cap having two closed compartments and a common tear-off foil for both compartments.

This embodiment is suited for integrated medication.

Figure 27A:
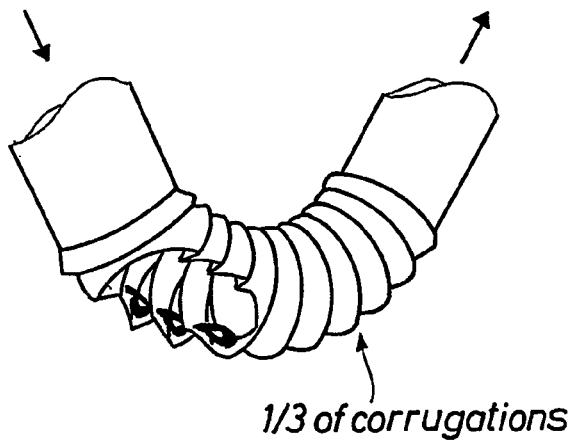
FIGS. 27a, 27b and 27c show the flow through the corrugated middle section of the tubular body.
Figure 27B:
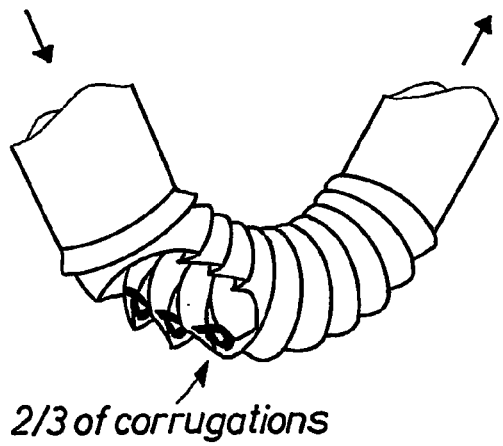
Figure 27C:
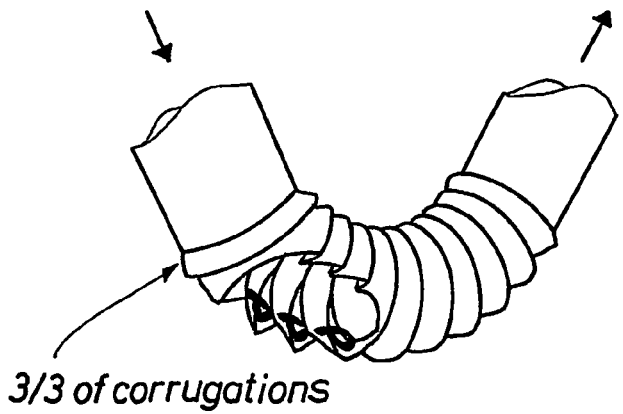
Figure 28:
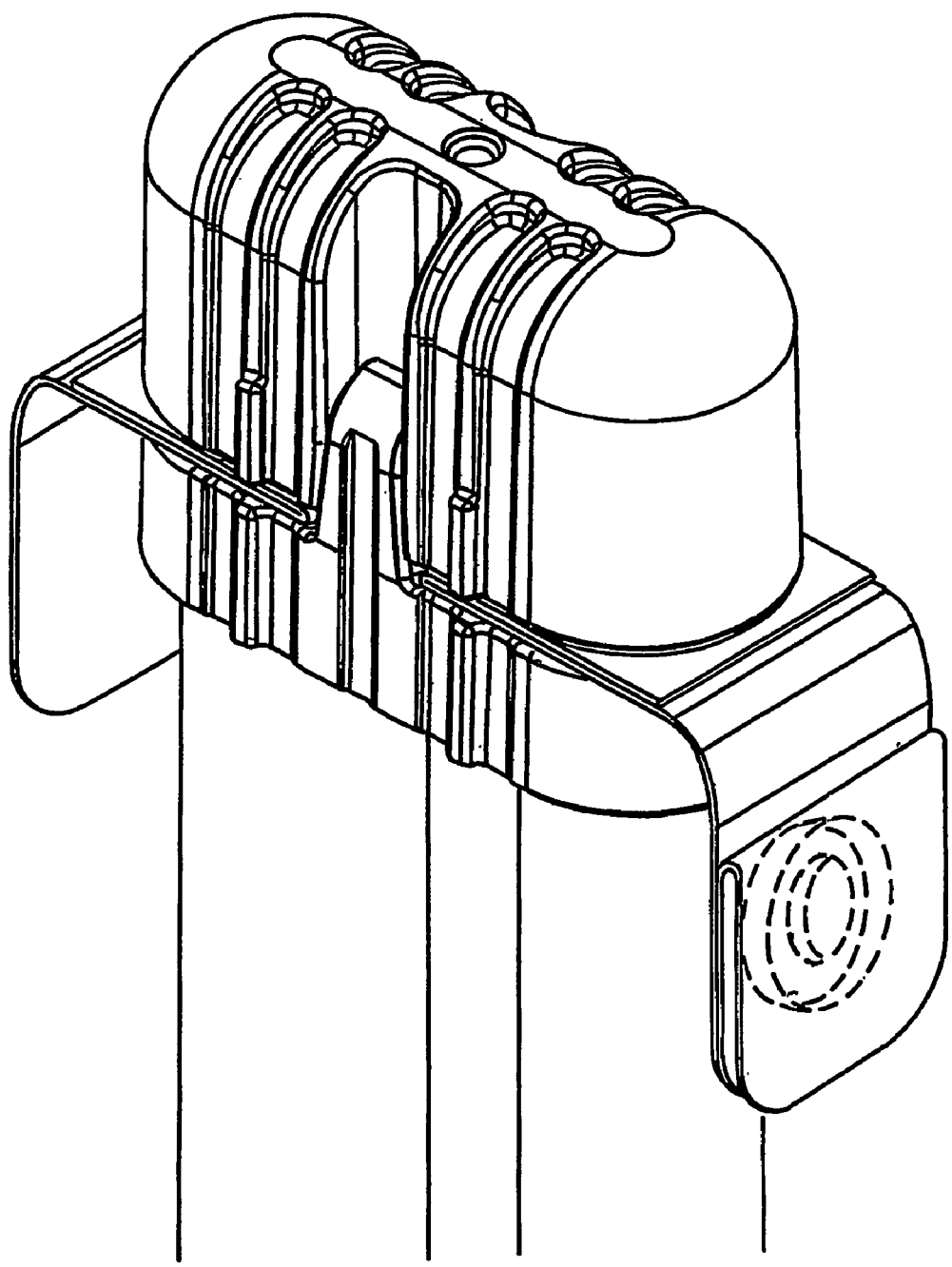
FIG. 28 shows an inhaler for pulmonary and nasal inhalation.
Figure 29:
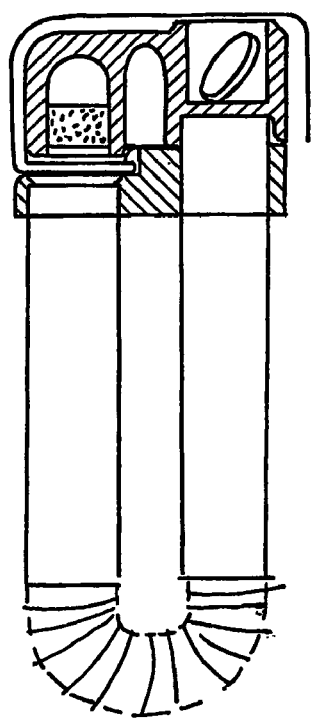
FIG. 29 shows an inhaler for pulmonary or nasal inhalation together with a closed compartment including a pill to be swallowed separately.
Figure 30:
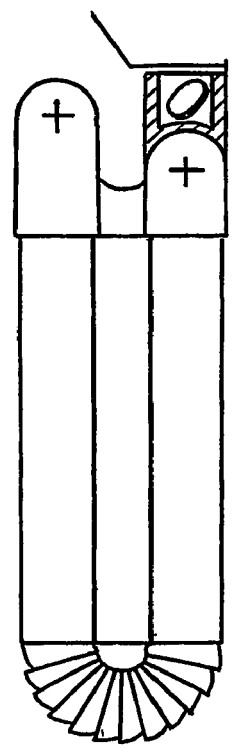
FIG. 30 shows an inhaler having a cap with a closed compartment including a pill to be swallowed separately.

FIGS. 27a, 27b and 27c show the flow through the corrugated bendable section of the tubular body after the particulate substance has been released from the cap at the beginning of the corrugations in the intake direction. As a result the lumps of the particulate substance due to the hittings of the step site of the corrugations are crushed and dispersed more and more every time they hit one of the succeeding corrugations. As a result a better powder dispersion is obtained than hitherto known, cf the following table, illustrating the influence of the corrugations.

Device Corrugation Study

The influence of the localisation of the powder in the whirl chamber was investigated. The selected powder formulation (cf Budesonide formulation study) was respectively located at the beginning (1/3, cf FIG. 27a), in the middle (2/3, cf FIG. 27b) and at the end (3/3, cf FIG. 27c) of the corrugation zone of the device with respect to the outlet portion.

The Fine Particle Dose (FPD) of the delivered dose from each corrugation zone was determined by using the MSLI. Table 1 summarises the test results for each localisation in the corrugation zone.

TABLE 1

Budesonide corrugation studies

| | | 1/3 of corrugation zone | 2/3 of corrugation zone | 3/3 of corrugation zone |
|---|---|---|---|---|
| Fine Particle Dose (FPD) | <5 μm [nm] | 41.9 | 40.2 | 49.0 |
| | <5 μm [%]* | 26.3 | 26.3 | 34.1 |
| Metered Dose (MSLI) | [μg Budesonide] | 170.4 | 165.2 | 161.5 |
| Delivered Dose (MSLI) | [μg Budesonide] | 158.9 | 152.6 | 143.8 |

The percentage refers to the delivered dose detected by MSLI

The conclusion is that:

The position of the drug in the device seems to influence the Fine Particle Dose (FPD).

The higher the number of corrugations touched the better the value for the FPD.

Between zone 1/3 and 2/3 no difference was noted.

Between zone 2/3 AND 3/3 a difference was noted.

The previous devices require the manufacturing equipment to perform pre-filling of the dose into the inhaler tube. According to the invention such handling has been simplified by instead doing pre-filling into the cap and subsequently sealing the cap. As a result, a higher production speed and lower handling costs have been obtained.

The invention has been described by way of several different embodiments. It is possible to make numerous alterations to the embodiments shown and described while staying within the scope of the invention.

The inhaler according to the invention may be used for nasal as well as pulmonary inhalation.

FIG. 28 shows an inhaler for both pulmonary and nasal inhalation. The inhaler comprises a cap with two closed compartments. Each compartment includes an active, inhalable, particulate substance. Each of the substances may be released separately by removing a separate tear-off foil. One of the released substances may be used for pulmonary inhalation. Thereafter, the substance in the other closed compartment may be released to the tubular body to be inhaled by nasal inhalation. As a result, a device for both pulmonary and nasal inhalation has been provided.

One of the tear-off foils may also be provided with a pill to be swallowed in a conventional manner.

FIG. 29 shows a device for pulmonary or nasal inhalation together with a closed compartment including a pill. The pill and the inhalable, particulate substance may be discharged simultaneously by removing a tear-off foil, which is common for the compartment including the pill and the compartment, including the particulate substance to be discharged into the U-formed tubular body.

FIG. 30 shows a device with a cap including a closed compartment for a pill to be swallowed separately.

The invention claimed is:

1. An inhaler comprising:

a tubular body having inlet and outlet ends defining a tubular air flow passage therebetween and a bendable generally U-shaped section having a region with peripherally extending corrugations forming a whirl chamber; and a cap attaching to the inlet and outlet ends of the tubular body and connecting said ends; and at least one closed compartment in communication with the cap and including a dose of at least one active inhalable particulate substance, the closed compartment including a sealable opening, such that when the sealable opening is opened, said particulate substance is dispensed from said closed compartment though the inlet end of the tubular body into the tubular flow passage at a beginning section of the corrugation region;

wherein when the user inhales air from the outlet end of the tubular air flow passage, the particulate substance is drawn through the corrugation region so that the particulate substance is suspended in the air inhaled by the user.

2. An inhaler according to claim 1, characterized in that the sealable opening is closed by a tear-off foil.

3. An inhaler according to claim 2, characterized in that the tear-off foil is composed of a laminate barrier foil.

4. An inhaler according to claim 3, characterized in that the laminate barrier foil is composed of a layer of aluminum covered by a layer of polypropylene on both sides.

5. An inhaler according to claim 2 characterized in that the tear-off foil is adapted to be removed after attaching an attachable part to the cap.

6. An inhaler according to claim 1, characterized in that the sealable opening is closed by a piercable foil, and that the tubular body is adapted to pierce said foil, when the cap is attached to said tubular body.

7. An inhaler according to claim 1, characterized in that the sealable opening is closed bending said tubular body, and that said sealable opening is opened by unbending said tubular body.

8. An inhaler according to claim 7, characterized in that the cap keeps the tubular body bent while not in use.

9. An inhaler according to claim 1, characterized in that the sealable opening is closed by a squeezing device therein squeezing together a part of the tubular body, the sealable opening being opened by removing the squeezing device.

10. An inhaler according to claim 1, characterized in that the closed compartment comprises a tube-like body, in which one end is permanently closed, and the other end is adapted to be inserted into the tubular body, said sealable opening being closed by means sticking a part of the walls of said tube-like body together, said sealable opening may be opened by a supplying pressure to or pulling at said tube-like body.

11. An inhaler according to claim 1, characterized in that the sealable opening is closed by a rotating, slidable element with at least one hole, where said rotating, slidable element has a first and a second position, and in said the position is adapted to close said sealable opening, and in the second position is adapted to open said sealable opening by communicating said closed compartment with said hole.

12. An inhaler according to claim 11, characterized in that the rotating, slidable element comprises friction elements, and that said friction elements are adapted to hold said rotating, slidable element in the first position, to produce some friction while said rotating, slidable element is rotated from said first position to said second position and fixate said rotating, slidable element at said second position.

13. An inhaler according to claim 1, characterized in that the cap is constructed from a soft, squeezable material, that the closed compartment is likewise constructed from a soft, squeezable material, and that said closed compartment is adapted to rupture along the sealable opening, when a pressure is applied to said cap.

14. An inhaler according to claim 1, characterized in that the material of the closed compartment is adapted in such a manner that when it ruptures, the material is not dispensed to the tubular body.

15. An inhalator according to claim 1 further comprising two or more tubular bodies wherein the cap is adapted to accommodate the two or more tubular bodies.

16. An inhaler according to claim 1, characterized in that the cap is in communication with two closed compartments, each compartment containing a separate, inhalable particulate substance.

17. An inhaler according to claim 3 characterized in that the tear-off foil is adapted to be removed after attaching an attachable part to the cap.

18. An inhaler according to claim 4 characterized in that the tear-off foil is adapted to be removed after attaching an attachable part to the cap.

* * * * *